US011680921B2

(12) United States Patent
BelBruno et al.

(10) Patent No.: US 11,680,921 B2
(45) Date of Patent: Jun. 20, 2023

(54) DIOL AND TRIOL SENSORS AND ASSOCIATED METHODS

(71) Applicant: FreshAir Sensor, LLC, Lebanon, NH (US)

(72) Inventors: Joseph J. BelBruno, Hanover, NH (US); Andrei Burnin, West Lebanon, NH (US); Katie Shelton, Lebanon, NH (US); Matthew Curtin, Lebanon, NH (US); Jacob Fisher, Lebanon, NH (US)

(73) Assignee: FreshAir Sensor, LLC, Lebanon, NH (US)

( * ) Notice: Subject to any disclaimer, the term of this patent is extended or adjusted under 35 U.S.C. 154(b) by 709 days.

(21) Appl. No.: 16/656,482

(22) Filed: Oct. 17, 2019

(65) Prior Publication Data

US 2020/0124556 A1 Apr. 23, 2020

Related U.S. Application Data

(60) Provisional application No. 62/747,590, filed on Oct. 18, 2018.

(51) Int. Cl.
*G01N 27/12* (2006.01)
*G01N 33/497* (2006.01)

(52) U.S. Cl.
CPC ......... *G01N 27/127* (2013.01); *G01N 27/126* (2013.01); *G01N 33/497* (2013.01); *G01N 2033/4975* (2013.01)

(58) Field of Classification Search
CPC .. G01N 27/127; G01N 27/126; G01N 33/497; G01N 2033/4975
See application file for complete search history.

(56) References Cited

U.S. PATENT DOCUMENTS

2008/0021339 A1* 1/2008 Gabriel ................. A61B 5/097
422/400
2016/0341685 A1* 11/2016 Yoshioka ........... G01N 33/5438

FOREIGN PATENT DOCUMENTS

EP 677288 A1 * 10/1995 ............... A61K 8/44
JP 2017187358 A * 10/2017
WO WO-2014115516 A1 * 7/2014 ........... A61B 5/1451

* cited by examiner

*Primary Examiner* — Christopher Adam Hixson
(74) *Attorney, Agent, or Firm* — Cozen O'Connor

(57) ABSTRACT

A sensor for sensing diols and triols includes (a) a substrate, (b) a conductive coating disposed on the substrate and having affinity for binding with a substance selected from the group consisting of diols, triols, and a combination thereof, and (c) two electrodes in contact with the conductive coating to probe conductivity of the conductive coating so as to detect the substance from a reduction in the conductivity. A method for detecting vaping includes (a) measuring conductivity of a conductive coating having affinity for binding with an airborne substance selected from the group consisting of diols, triols, and a combination thereof, and (b) detecting presence of the airborne substance as a decrease in the conductivity.

18 Claims, 7 Drawing Sheets

400

```
┌─────────────────────────────────────────────────────────────────────────────┐
│ MEASURE CONDUCTIVITY OF A CONDUCTIVE COATING HAVING AFFINITY FOR BINDING WITH AN │
│ AIRBORNE SUBSTANCE SELECTED FROM THE GROUP CONSISTING OF DIOLS, TRIOLS, AND A    │
│                           COMBINATION THEREOF                                │
│                                    410                                       │
└─────────────────────────────────────────────────────────────────────────────┘
                                       │
                                       ▼
┌─────────────────────────────────────────────────────────────────────────────┐
│       DETECT PRESENCE OF THE AIRBORNE SUBSTANCE AS A DECREASE IN THE CONDUCTIVITY │
│                                    420                                       │
│  ┌──────────────────────────────────┐  ┌──────────────────────────────────┐ │
│  │ DETECT A DECREASE IN CONDUCTIVITY│  │ DETECT A DECREASE IN CONDUCTIVITY│ │
│  │ CAUSED BY HYDROXYL-GROUP PAIRS OF│  │ CAUSED BY HYDROXYL-GROUP PAIRS OF│ │
│  │ RESPECTIVE MOLECULES OF THE      │  │ MOLECULES OF THE AIRBORNE        │ │
│  │ AIRBORNE SUBSTANCE REACTING AND  │  │ SUBSTANCE INTERACTING WITH       │ │
│  │ COVALENTLY BONDING WITH THE      │  │ POLYMER CHAINS OF THE CONDUCTIVE │ │
│  │ CONDUCTIVE COATING               │  │ POLYMER TO DISRUPT ELECTRON      │ │
│  │              422                 │  │ DISTRIBUTION OF THE POLYMER CHAINS│ │
│  │                                  │  │              424                 │ │
│  └──────────────────────────────────┘  └──────────────────────────────────┘ │
└─────────────────────────────────────────────────────────────────────────────┘
                                       │
                                       ▼
┌─────────────────────────────────────────────────────────────────────────────┐
│           OUTPUT INDICATION OF DETECTION OF THE AIRBORNE SUBSTANCE           │
│                                    430                                       │
└─────────────────────────────────────────────────────────────────────────────┘
```

FIG. 4

DIOL AND TRIOL SENSORS AND ASSOCIATED METHODS

CROSS-REFERENCE TO RELATED APPLICATIONS

The present application claims the benefit of priority from U.S. Patent Application Ser. No. 62/747,590, filed on Oct. 18, 2018, which is incorporated herein by reference in its entirety.

BACKGROUND

A diol is an organic chemical compound that has two hydroxyl (OH) groups, and a triol is an organic chemical compound that has three hydroxyl groups. The hydroxyl groups are functional groups that enable the chemical compound to participate in certain types of chemical reactions and form certain types of bonds with other chemical compounds.

An electronic cigarette is a handheld, electronic device that heats and aerosolizes a nicotine-containing liquid "vape solution" to form a vapor. The vape solution typically includes propylene glycol (a diol) and/or glycerol (a triol) to help form the vapor and thus serve as a carrier for the nicotine. Electronic cigarettes have been touted as a healthier alternative to conventional cigarette smoking and as a tool to help cigarette smokers quit smoking. However, after their initial introduction, the use of electronic cigarettes has quickly expanded to other groups than cigarette smokers addicted to nicotine. "Vaping" devices are used to inhale marijuana vapor as well as nicotine vapor, and nicotine vaping in particular is now used by populations that likely would not have taken up the use of nicotine in any other form.

Compact vaping devices (e.g., Juul devices from Juul Labs) with flavored nicotine solution (for example as provided in Juul pods) are in widespread use among teenagers, thus creating nicotine addiction in a group that has not already picked up smoking of conventional cigarettes. In addition to nicotine addiction, there is growing concern over the health impact of other compounds known to be in the vapor, such as certain carcinogenic organic compounds and heavy metals. Also, although propylene glycol is generally considered non-toxic, studies have shown that propylene glycol (typically a primary vapor component), when heated to form the vapor, may produce the carcinogen propylene oxide. Recently, use of the products has led to several deaths for reasons not understood at the present time.

The use of compact vaping devices, such as Juul devices, is easily concealed. The devices are the size of a thumb drive, and their use leaves no lingering cigarette smoke or cigarette breath.

SUMMARY

One aspect of the present invention includes the realization that a sensor for detecting vaping can be a valuable tool in stopping and preventing the use of vaping and thus limit the harmful effects thereof. Another aspect of the present invention includes the realization that real-time sensing of these compounds would be desirable to quickly and accurately sense vaping. The present embodiments provide real-time sensing of vaping. One aspect of the present embodiments is based on our discovery that certain sensing-compatible materials have specific affinity for binding with diols and triols, such as those found in the vapor from vaping products, and that these sensing materials have response time that allow for real-time detection. Another aspect of the present embodiments is our discovery that molecular imprinting of these sensing materials is not needed to achieve the specific affinity.

In an embodiment, a sensor for sensing diols and triols includes (a) a substrate, (b) a conductive coating disposed on the substrate and having affinity for binding with a substance selected from the group consisting of diols, triols, and a combination thereof, and (c) two electrodes in contact with the conductive coating to probe conductivity of the conductive coating so as to detect the substance from a reduction in the conductivity.

In an embodiment, a method for detecting vaping includes (a) measuring conductivity of a conductive coating having affinity for binding with an airborne substance selected from the group consisting of diols, triols, and a combination thereof, and (b) detecting presence of the airborne substance as a decrease in the conductivity.

BRIEF DESCRIPTION OF THE DRAWINGS

FIG. 4 illustrates one method for detecting vaping, according to an embodiment.

DESCRIPTION OF EXAMPLE EMBODIMENTS

Figure 1:
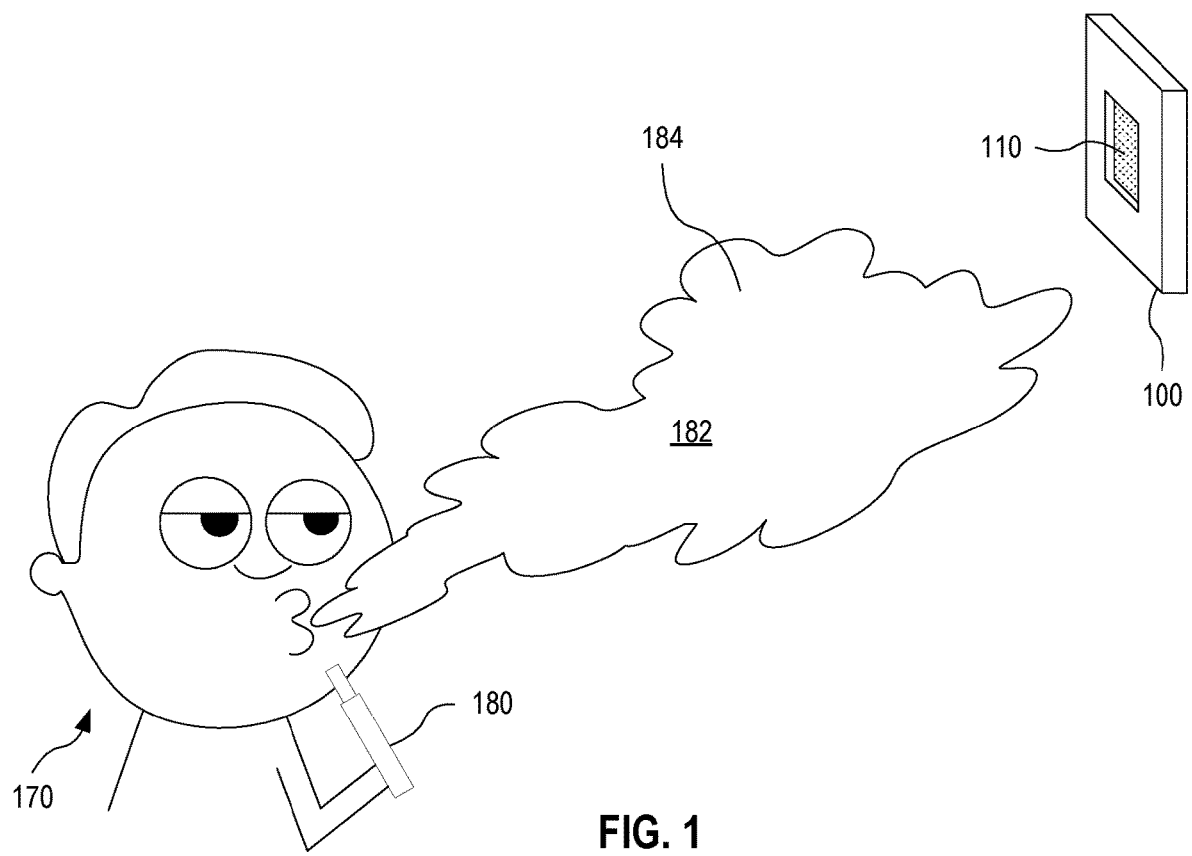
FIG. 1 illustrates, in an example use scenario, a sensor for sensing diols and triols, according to an embodiment.

FIG. 1 illustrates one sensor 100 for sensing diols and triols. Sensor 100 includes a conductive coating 110 that has affinity for binding with substances 184 belonging to the group consisting of diols, triols, and a combination thereof. In one embodiment, conductive coating 110 has affinity for binding with all diols and triols, or a variety of diols and triols, although the strength of the affinity may depend on the type of diol/triol. FIG. 1 shows sensor 100 in an example use scenario, wherein sensor 100 detects vaping by a user 170 of a vaping device 180. Vapor 182 exhaled by user 170 includes a substance 184 which is detected by sensor 100 when substance 184 binds to conductive coating 110. Sensor 100 may thus detect, e.g., propane-1,2-diol (propylene glycol), propane-1,3-diol (beta-propylene glycol), and/or glycerol, all of which are common components of vapor from vaping devices.

When sensor 100 is used as a vaping sensor, substance 184 is airborne, although substance 184 may be deposited on conductive coating 110 in the form of vapor droplets. Without departing from the scope hereof, sensor 100 may instead be used to sense substance 184 in a liquid sample.

Advantageously, the response time of sensor 100 allows for real-time detection of substance 184 and sensor 100 may thus be used to detect vaping, which is otherwise easily concealed. Sensor 100 is based on our discovery that certain sensing-compatible materials have specific affinity for binding with diols and triols. Advantageously, molecular imprinting of the materials is not required to achieve this specific affinity.

Figure 2:
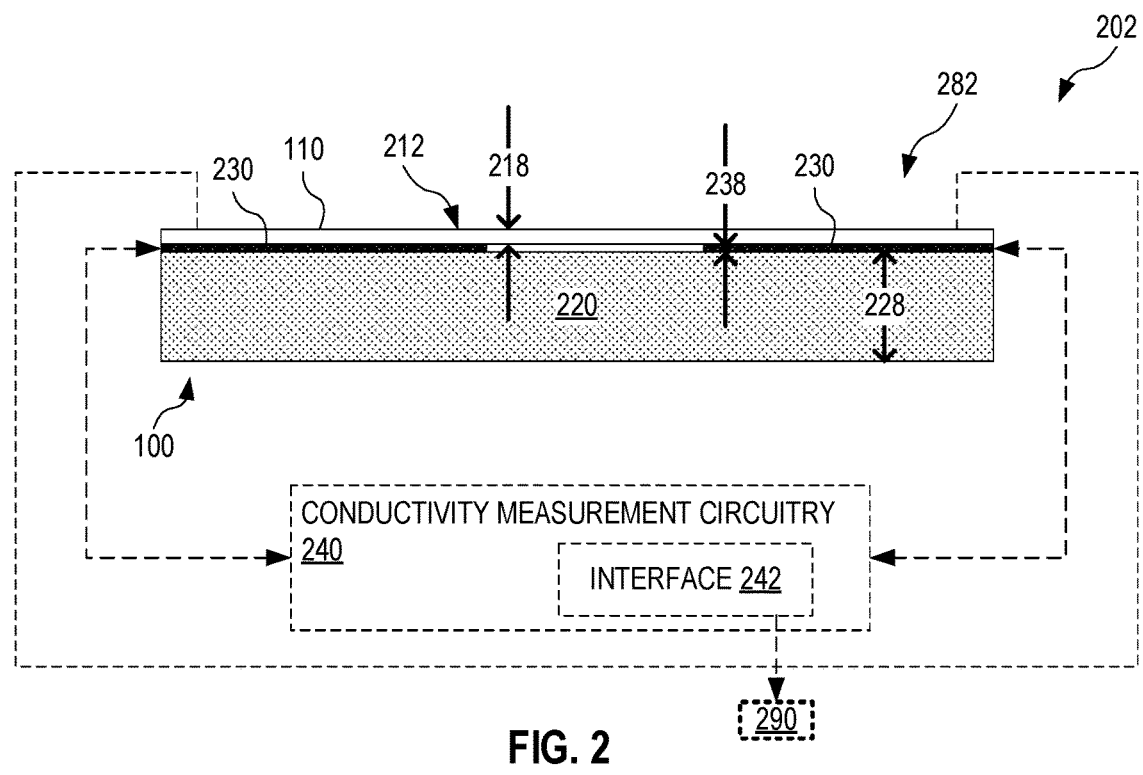
FIG. 2 shows the sensor of FIG. 1 in further detail.

FIG. 2 shows sensor 100 in further detail. Sensor 100 includes a substrate 220, two electrodes 230, and conductive coating 110. Conductive coating 110 and electrodes 230 are disposed on substrate 220. Electrodes 230 are in contact with conductive coating 110 to probe the conductivity of conductive coating 110. The conductivity of conductive coating 110 is reduced by binding of substance 184 thereto, and sensor 100 may therefore detect vaping (or the presence of substance 184 for other reasons than vaping) as a decrease in the conductivity of conductive coating 110.

Although depicted in FIG. 2 as being located between conductive coating 110 and substrate 220, electrodes 230 may, without departing from the scope hereof, be located elsewhere as long as electrodes 230 are in contact with conductive coating 110. In one example, electrodes 230 are disposed on a top surface 212 of conductive coating 110 facing away from substrate 220. In another example, one electrode 230 is disposed on top surface 212 and the other electrode 230 is disposed between substrate 220 and conductive coating 110.

Sensor 100 may be implemented in a sensing module 202 together with conductivity measurement circuitry 240 electrically coupled to each electrode 230. In one implementation of this embodiment, conductivity measurement circuitry 240 applies a direct current (DC) voltage drop between electrodes 230 and measure a resulting DC current flowing through at least a portion of conductive coating 110 from one electrode 230 to the other electrode 230. In another implementation of this embodiment, conductivity measurement circuitry 240 is configured as an ohmmeter and measures the resistance of conductive coating 110. For the purpose of the present disclose, conductivity measurement and resistance measurement are both valid measures of the conductivity of a material. Conductivity measurement circuitry 240 may include an interface 242 that outputs a sensing output 290. Sensing output 290 may include one or more of (a) a conductivity of conductive coating 110, (b) a concentration of substance 184 detected by sensor 100, wherein the concentration is derived from the conductivity of conductive coating 110, (c) an indication that the conductivity of conductive coating 110 has decreased from a baseline level, and/or (d) an indication that the conductivity of conductive coating 110 has decreased by an amount that corresponds to an above-threshold presence of substance 184.

Alternatively, sensor 100 is instead configured to cooperate with external conductivity measurement circuitry, for example provided by a third party.

Conductive coating 110 has thickness 218. Conductive coating 110 may be a continuous polymer film, a nanofiber mat, a collection of nanoparticles, or a combination thereof. Herein, a "continuous polymer film" refers to a film predominantly composed of a polymer and having no significant density structure. A continuous polymer film may be produced by dissolving a polymer in a liquid and disposing the resulting solution on a substrate.

In one embodiment, thickness 218 is in the range between 20 nanometers and 5 microns. A thin conductive coating 110 may allow for more uniform dispersion of substance 184 therein, such that binding of substance 184 to conductive coating 110 has greater effect on the conductivity of conductive coating 110. On the other hand, a thicker conductive coating 110 may be more practical from a manufacturing perspective. Also, in embodiments where electrodes 230 are disposed between substrate 220 and conductive coating 110, conductive coating 110 may be at least partly suspended between electrodes 230, in which case a thicker conductive coating 110 may be more robust against breakage. In certain embodiments, thickness 218 is in the range between 20 nanometers and 1.0 microns.

Substrate 220 is a dielectric material such as silicon dioxide, glass, or printed circuit board. Electrodes 230 are for example metallic. In one embodiment, electrodes 230 are deposited on substrate 220 using photolithography. Electrodes 230 may be chromium electrodes, optionally with a nickel and/or gold overlay between the chromium and conductive coating 110. Electrodes 230 may have thickness 238 in the range between 50 and 200 nanometers. Substrate 220 has thickness 228 sufficient to provide structural stability for electrodes 230 and conductive coating 110. Thickness 228 may be in the range from 0.5 to 2.0 millimeters.

Sensing module 202 may further include an enclosure 280 having an opening 282 that allows exposure of conductive coating 110 to the ambient environment.

Figure 3:
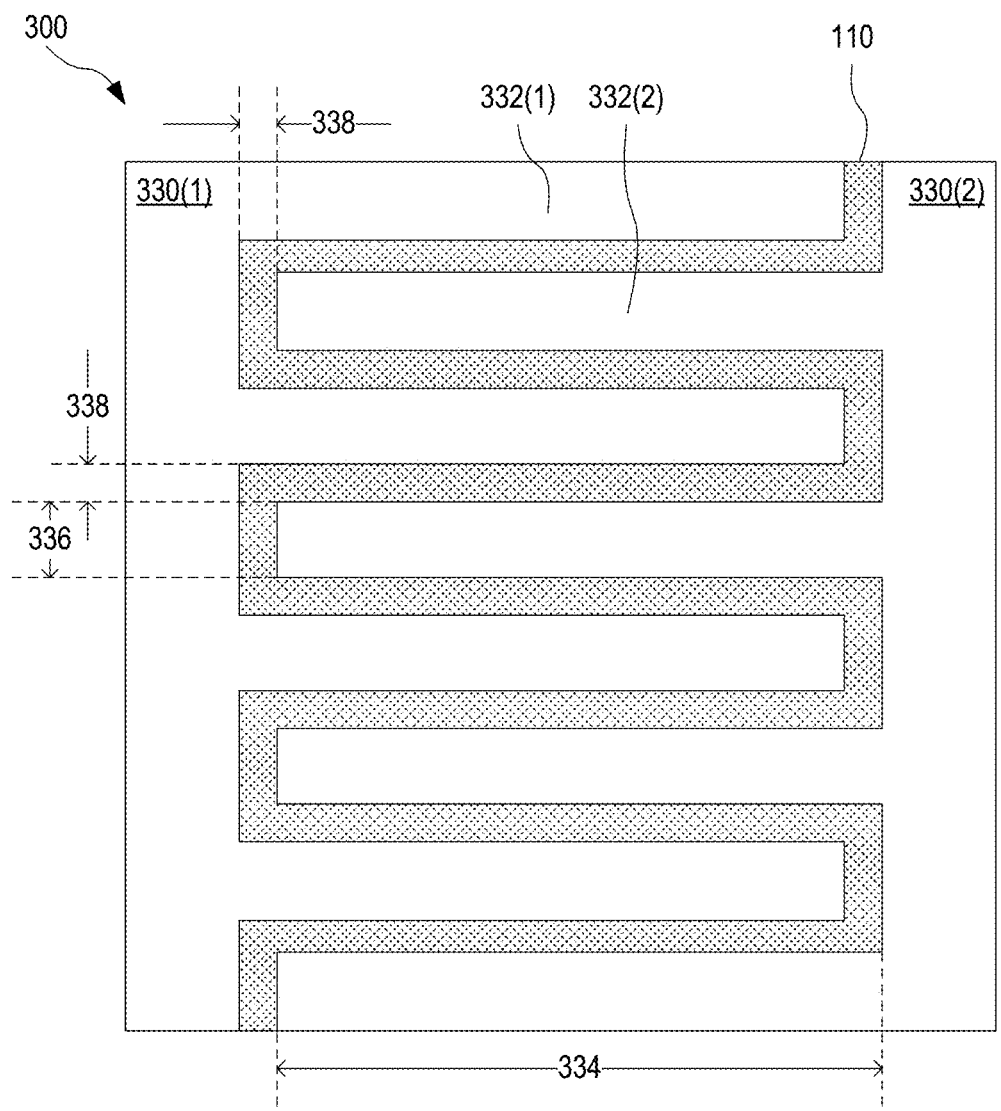
FIG. 3 illustrates an interdigitated electrode configuration, according to an embodiment.
Figure 5:
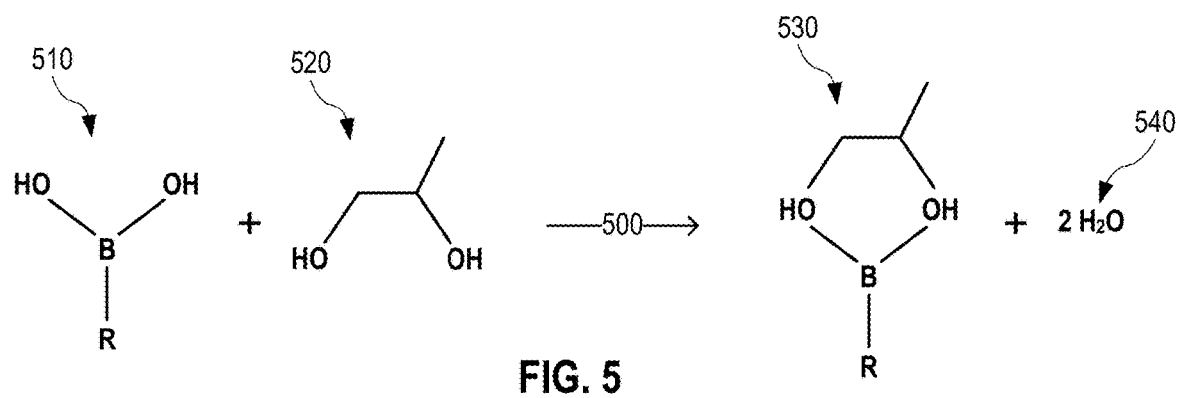
FIG. 5 illustrates reaction between boronic acid and propylene glycol to form a covalently bonded reaction product, according to an embodiment.
Figure 6:
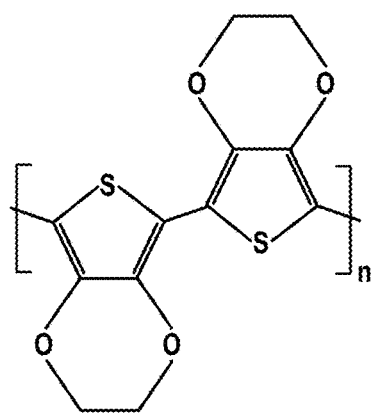
FIG. 6 shows the molecular structure of PEDOT.
Figure 7:
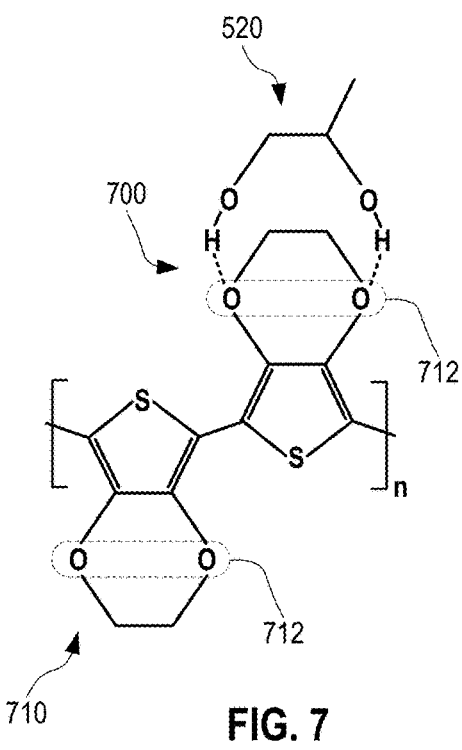
FIG. 7 illustrates interaction between PEDOT and propylene glycol, according to an embodiment.
Figure 8:
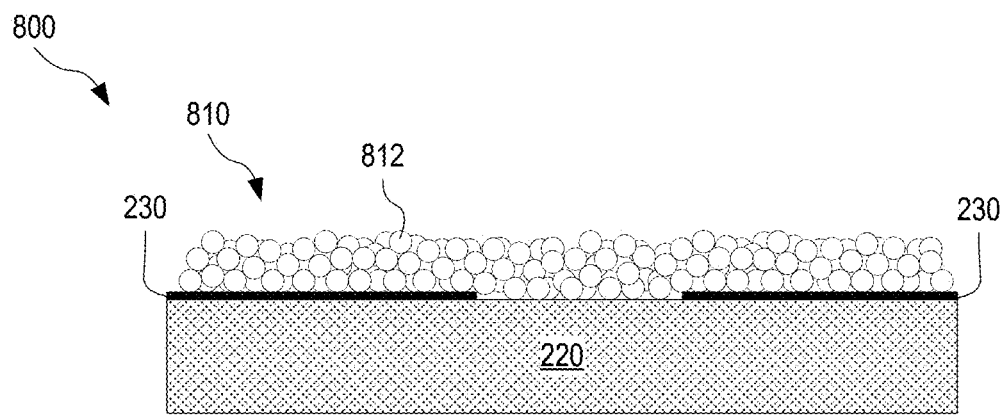
FIG. 8 illustrates a nanoparticle-based sensor for sensing diols and triols, according to an embodiment.
Figure 9:
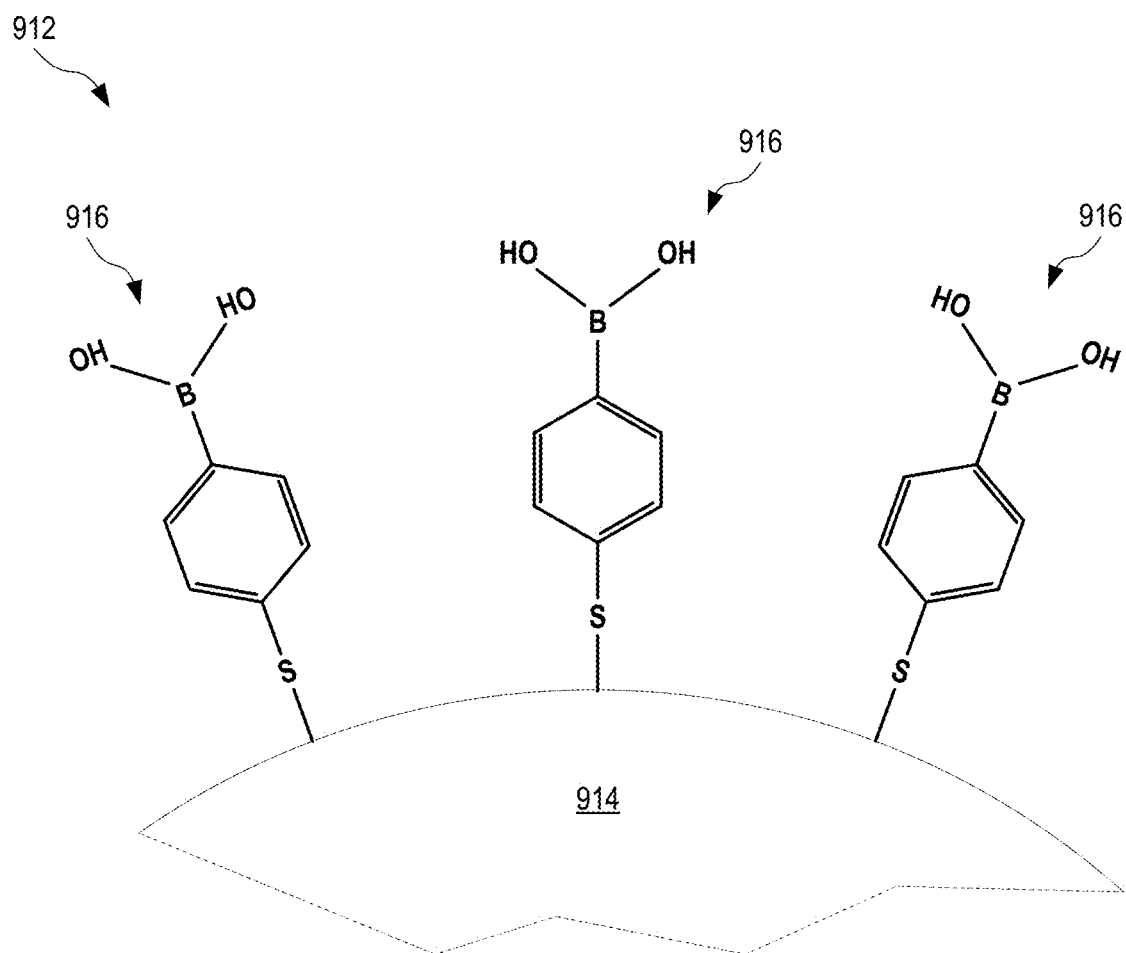
FIG. 9 schematically illustrates a functionalized nanoparticle having affinity for binding with diols and triols, according to an embodiment.

FIG. 3 illustrates one interdigitated electrode configuration 300 of electrodes 330 in an embodiment of sensor 100. Electrodes 330 are embodiments of electrodes 230. Each electrode 330 forms a plurality of fingers 332. Fingers 332(1) or electrode 330(1) are interdigitated with fingers 332(2) of electrode 330(2). Interdigitated electrode configuration 300 ensures good spatial averaging of the local conductivity of portions of conductive coating 110 spanning between electrodes 330(1) and 330(2). For comparison, if two smaller electrodes are positioned far apart from each other on conductive coating 110 and the binding of substance 184 to conductive coating 110 is not uniform, the measured conductivity may be dominated by one or more high-conductivity paths associated with regions of conductive coating 110 having less of substance 184 bound thereto.

Each finger 332 has width 336, and length 334. Width 336 is for example in the range from 10 to 100 microns, such as approximately 40 microns. Length 334 is for example in the range from 0.5 to 3 centimeters, such as approximately 2 centimeters. Adjacent fingers 332 are spaced apart from each other by a spacing 338. Spacing 338 is for example in the range from 5 to 50 microns, such as approximately 20 microns. Each electrode 330 may include between 50 and 300 fingers 332.

FIG. 4 illustrates one method 400 for detecting vaping. Method 400 includes steps 410 and 420. Method 400 may be performed by sensing module 202. Step 410 measures the conductivity of a conductive coating having affinity for binding with an airborne substance selected from the group consisting of diols, triols, and a combination thereof. In one example of step 410, conductivity measurement circuitry 240 measures the conductivity of conductive coating 110 between electrodes 230.

Step 420 detects the presence of the airborne substance as a decrease in the conductivity measured in step 410. In one example of step 420, conductivity measurement circuitry 240 measures a decreased conductivity of conductive coating 110 between electrodes 230 caused by substance 184 bound to conductive coating 110.

In one embodiment, step 420 includes a step 422. Step 422 detects a decrease in conductivity of the conductive coating, wherein the decrease is caused by hydroxyl-group pairs, of respective molecules of the airborne substance, covalently bonding with the conductive coating. Herein, a "hydroxyl-group pair" refers to a pair of hydroxyl groups of the same diol or of the same triol. For example, the two hydroxyl groups of a single propylene glycol molecule or a single beta-propylene glycol molecule form a hydroxyl-group pair, and two of the three hydroxyl groups of a single glycerol molecule form a hydroxyl-group pair. In the case of triols, any two of the three hydroxyl groups of the triol may form the pair. However, the conductive coating may have stronger affinity for bonding with pairs of hydroxyl groups that are closest to each other in the triol. In one example of step 422, conductive coating 110 includes a compound, such as boronic acid, capable of forming covalent bonds with a pair of hydroxyl groups in close proximity to each other. In this example, covalent binding between this compound and hydroxyl-group pairs of molecules airborne substance 184 reduces the conductivity of conductive coating 110.

In another embodiment, step 420 includes a step 424. Step 424 detects a decrease in conductivity of the conductive coating, wherein the decrease is caused by hydroxyl-group pairs, of respective molecules of the airborne substance, interacting with polymer chains of the conductive polymer to disrupt the conductivity of the polymer chains. In one example of step 424, conductive coating 110 includes polymer chains, and hydroxyl-group pairs of molecules of airborne substance 184 interact with the polymer chains to disturb their ability to conduct a current. The polymer chains may be linear polymer chains such as poly(3,4-ethylenedioxythiophene), also referred to as "PEDOT".

Method 400 may further include a step 430 of outputting an indication of the detection of the airborne substance. In one example of step 430, conductivity measurement circuitry 240 outputs sensing output 290 via interface 242.

FIG. 5 illustrates one reaction 500 between boronic acid 510 and propylene glycol 520 to form a covalently bonded reaction product 530. Reaction 500 is an example of a reaction that leads to the conductivity decrease measured in step 422 of method 400. In reaction 500, the hydroxyl-group pair of propylene glycol 520 reacts with the hydroxyl-group pair of boronic acid to form covalently bonded reaction product 530 and, as a byproduct, two water molecules 540. By virtue of having hydroxyl-group pairs, beta-propylene glycol and glycerol are also capable of reacting with boronic acid 510 according to reaction 500.

In one embodiment of sensor 100, conductive coating 110 includes a conductive material and boronic acid, so as to have affinity for binding with diols and triols such as propylene glycol, beta-propylene glycol, and glycerol through reaction 500. This embodiment of sensor 100 may be used in an embodiment of method 400 implementing step 422. In this embodiment of sensor 100, the conductive material of conductive coating 110 may be composed of or include metal nanoparticles, nanofibers, carbon nanotubes, a polymer, and/or a combination thereof. The conductive material may be functionalized with boronic acid. For example, conductive coating 110 may be composed of or include metal nanoparticles functionalized with boronic acid.

Other similar acids, such as carbonic acid and sulfuric acid, may be considered as alternatives to boronic acid. However, in our experimental studies, an example of sensor 100 using an example of conductive coating 110 consisting of metal-nanoparticles functionalized with boronic acid showed a strong response (decrease in conductivity) to propylene glycol, whereas a conductive coating consisting of metal-nanoparticles functionalized with carbonic acid failed to produce a measurable response.

FIG. 6 shows the molecular structure of PEDOT. PEDOT is a linear polymer chain that repeats the structure depicted inside the square brackets of FIG. 6. PEDOT carries a positive charge.

FIG. 7 illustrates interaction 700 between PEDOT 710 and propylene glycol 520, wherein the hydroxyl-group pair of propylene glycol 520 interacts with a pair 712 of oxygen atoms of a segment of PEDOT 710. We speculate that interaction 700 disrupts the ability of PEDOT to conduct current along the length of the polymer chain. It is understood that any of the oxygen-pairs 712 of PEDOT may interact with the hydroxyl-group pair of propylene glycol 520 as shown for one oxygen-pair 712 in FIG. 7. The decrease in conductivity of PEDOT is expected to grow with the number of propylene glycol molecules interacting therewith according to interaction 700. By virtue of having hydroxyl-group pairs, beta-propylene glycol and glycerol are capable of interacting with PEDOT according to interaction 700.

In one embodiment of sensor 100, conductive coating 110 includes PEDOT, so as to have affinity for binding with diols and triols, such as propylene glycol, beta-propylene glycol, and glycerol, through interaction 700. Since PEDOT carries a positive charge, this embodiment of conductive coating 110 further includes a negatively charged polymer, such as polystyrene sulfonate (PSS). PEDOT and the negatively charged polymer may form a macromolecular salt. Embodiments of sensor 100 based on a PEDOT-containing embodiment of conductive coating 110 may be used in an embodiment of method 400 implementing step 424. To further enhance the response to bonding with diols and triols, the PEDOT-containing embodiment of conductive coating 110 may further include boronic acid.

FIG. 8 illustrates one nanoparticle-based sensor 800 for sensing diols and triols. Sensor 800 is an embodiment of sensor 100, wherein conductive coating 110 is implemented as a coating 810 of functionalized conductive nanoparticles 812. Nanoparticles 812 are functionalized to have affinity for binding with substance 184. In one embodiment, nanoparticles 812 are functionalized with a molecule, such as boronic acid 512, having affinity for reacting with hydroxyl-group pairs of diols and triols according to reaction 500. Sensor 800 may be used to perform an embodiment of method 400 that implements step 422. Nanoparticles 812 may be functionalized metal nanoparticles, for example made from gold, silver, and/or platinum. Alternatively, nanoparticles 812 may be functionalized polymer nanoparticles, made from a conductive polymer. Nanoparticles 812 may be between 1 and 100 nanometers in size. In one example, each nanoparticle 812 is an approximately spherical metal nanoparticle having a diameter in the range between 1 and 100 nanometers.

FIG. 9 schematically illustrates one functionalized nanoparticle 912 having affinity for binding with diols and triols. Functionalized nanoparticle 912 includes a metal nanoparticle 914 functionalized with 4-mercaptophenylboronic acid molecules 916. Functionalized nanoparticle 912 is an embodiment of nanoparticle 812. 4-mercaptophenylboronic acid molecules 916 are examples of boronic acid 510.

Referring again to FIG. 8, sensor 800 may be formed by suspending non-functionalized metal nanoparticles (e.g., metal nanoparticles 914) in a solution containing functionalization molecules (e.g., 4-mercaptophenylboronic acid molecules 916 or another boronic acid 510), drop casting the suspension on substrate 220 over electrodes 230, and evaporating the solvent to leave a coating of functionalized nanoparticles (e.g., functionalized nanoparticles 912 or another type of functionalized nanoparticles 812). In one example, the non-functionalized metal nanoparticles are surface-passivated, for example with citrate, prior to suspension in the solution containing functionalization molecules. When suspended in this solution, the functionalization molecules replace at least some of the surface-passivation molecules. In an alternative process, the nanoparticles are pre-functionalized such that the suspension solution does not need to include functionalization molecules.

Figure 10:
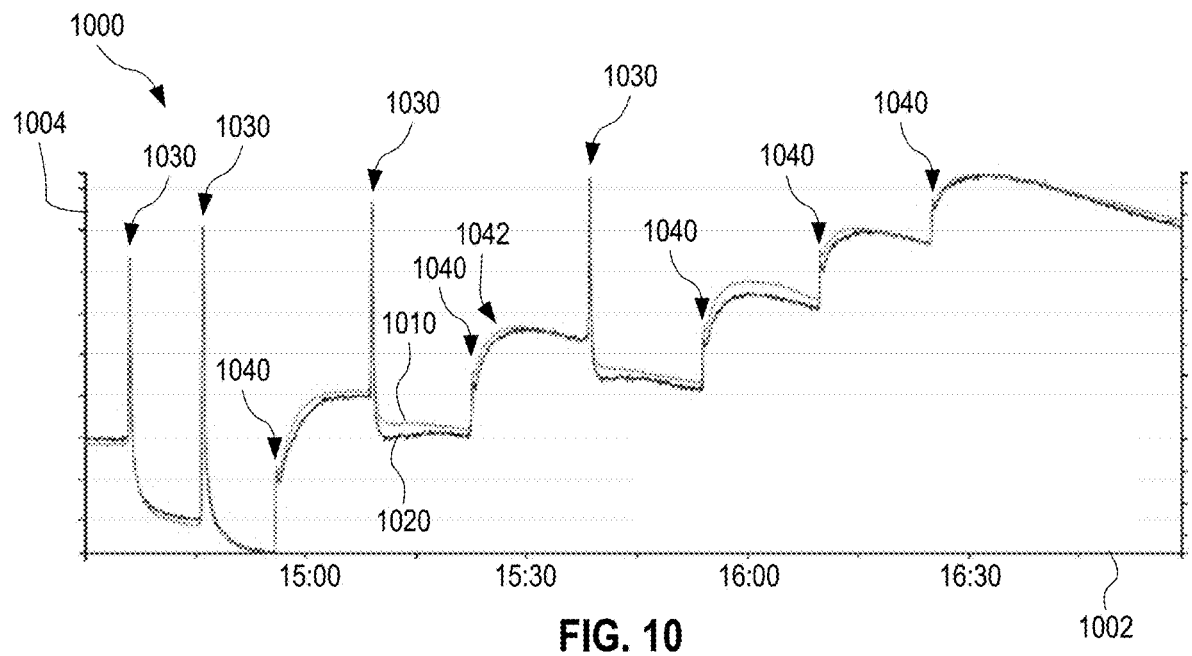
FIG. 10 is a plot of response of a nanoparticle-based sensor when exposed to propylene glycol and vapor from a mango-flavored JUUL pod, according to an embodiment.

FIG. 10 is a plot 1000 of response of a nanoparticle-based sensor when exposed to propylene glycol and vapor from a mango-flavored JUUL pod. Plot 1000 plots the resistance 1004 as a function of time 1002 for two nominally identical sensors, respectively represented by curves 1010 and 1020. These two sensors are examples of sensor 800 implementing functionalized nanoparticles 912 and interdigitated electrodes 330. Plot 1000 was obtained according to an embodiment of method 400.

Several features are noticeable in curves 1010 and 1020. Peaks 1030 are in response to exposure of the sensors to vapor from 20 microliters of propylene glycol. Sharp rises 1040 are in response to vapor from 20 microliters of mango-flavored JUUL "juice". Each sharp rise 1040 is followed by a slower rise 1042. It is evident that both sensors respond measurably and instantaneously to exposure of both pure propylene glycol and vapor from a JUUL pod. In addition, the two sensors show very similar response, indicating that the manufacturing and measuring processes are reliable.

Each nanoparticle-based sensor, associated with the data of plot 1000, was made by suspending citrate-passivated gold nanoparticles in a solution containing 4-mercaptophenylboronic acid. More specifically, 50 milliliters of boronic acid solution was prepared using 50 milligrams of boronic acid in water. The boronic acid solution was made basic before mixing this solution with 100 milliliters of a gold nanoparticle solution. The gold nanoparticle solution contained citrate-passivated gold nanoparticles at a concentration of 1 millimolar. The resulting suspension was drop cast onto a printed circuit board over a pair of interdigitated metal electrodes already formed thereon. After evaporation of the water, the functionalized gold nanoparticles formed a coating approximately 50 nanometers thick. The gold nanoparticles were approximately 15 nanometers in size.

Figure 11:
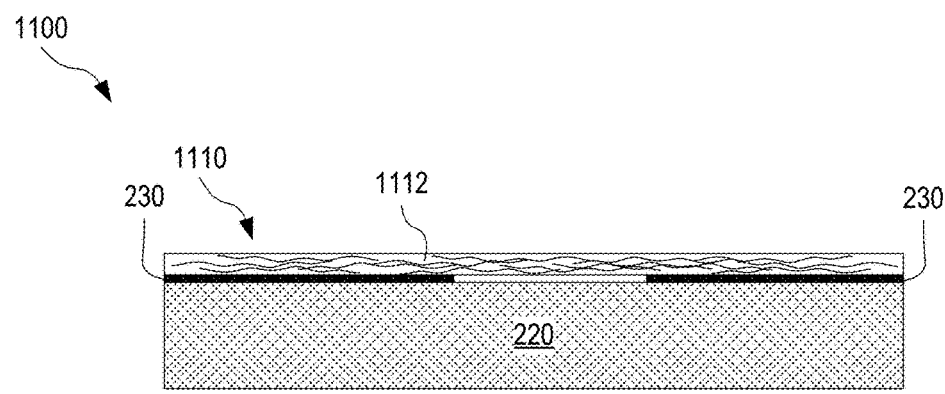
FIG. 11 illustrates a PEDOT-based sensor for sensing diols and triols, according to an embodiment.

FIG. 11 illustrates one PEDOT-based sensor 1100 for sensing diols and triols. Sensor 1100 is an embodiment of sensor 100, wherein conductive coating 110 is implemented as a polymer coating 1110. Polymer coating 1110 includes PEDOT chains 1112 (not necessarily aligned to each other as depicted in FIG. 11). Polymer coating 1110 further includes a negatively charged polymer, such as PSS. Polymer coating 1110 may be continuous polymer film. In certain embodiments, polymer coating 1110 also includes a humectant, such as glycerol triacetate, to increase the sensitivity of sensor 1100.

Sensor 1100 may be used to perform an embodiment of method 400. Without being bound by theory, diols and triols may interact with PEDOT according to interaction 700, and this embodiment of method 400 may thus implement step 424.

Sensor 1100 may be formed by solubilizing PEDOT and a negatively charged polymer (e.g., PSS) in a solvent, depositing the resulting solution on a substrate (for example with electrodes already formed thereon), and evaporating the solvent to form a continuous polymer film. The deposition may be done through, e.g., drop casting, spin casting, dip casting, ink-jet printing, or drawing with a plotter.

Figure 12:
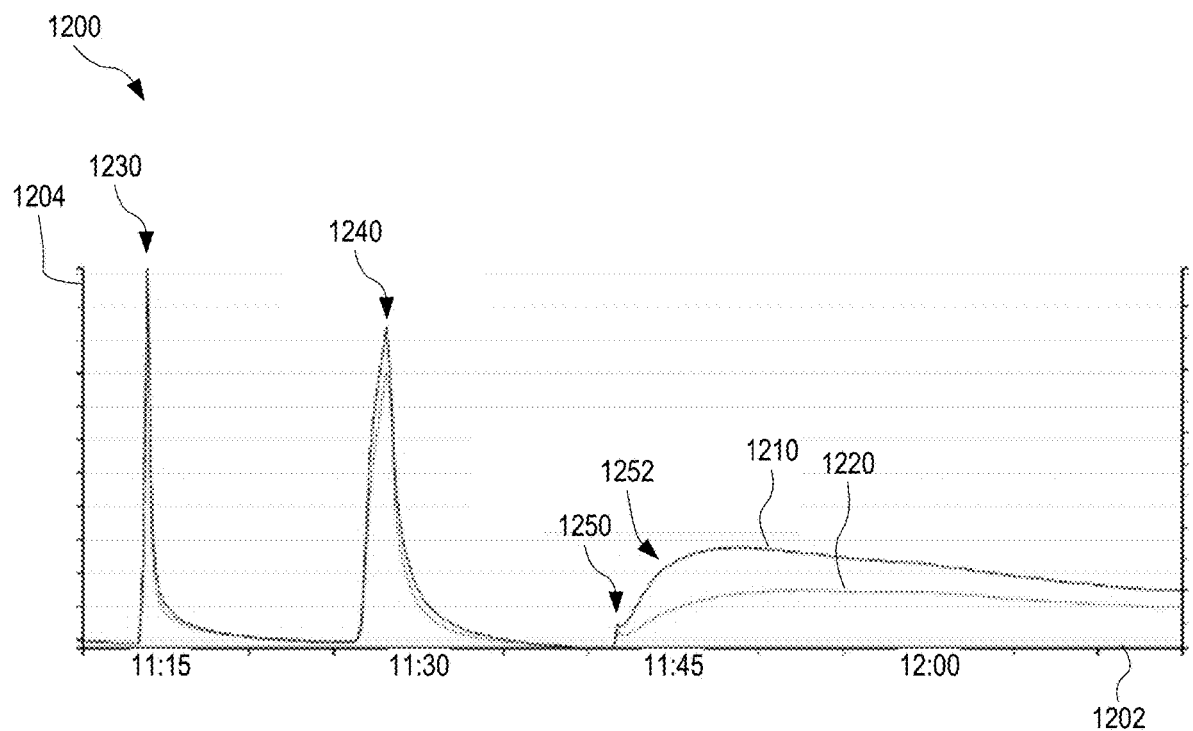
FIG. 12 is a plot of response of a PEDOT-based sensor when exposed to propylene glycol, beta-propylene glycol, and vapor from a Virginia-tobacco-flavored JUUL pod.

FIG. 12 is a plot 1200 of response of a PEDOT-based sensor when exposed to propylene glycol, beta-propylene glycol, and vapor from a Virginia-tobacco-flavored JUUL pod. Plot 1200 plots the resistance 1204 as a function of time 1202 for two nominally identical sensors, respectively represented by curves 1210 and 1220. These two sensors are examples of sensor 1100 implementing (a) polymer coating 1110 as a continuous polymer film composed of PEDOT:PSS and glycerol triacetate and (b) interdigitated electrodes 330. Plot 1200 was obtained according to an embodiment of method 400

Peak 1230 is in response to exposure of the sensors to vapor from 20 microliters of propylene glycol. Peak 1240 is in response to exposure of the sensors to vapor from 20 microliters of beta-propylene glycol. A sharp rise 1250 followed by a slower rise 1252 is in response to vapor from 5 microliters of Virginia-tobacco-flavored JUUL "juice". It is evident that both sensors respond measurably and instantaneously to exposure of each of pure propylene glycol, pure beta-propylene glycol, and vapor from a JUUL pod. In addition, the two sensors show very similar response, indicating that the manufacturing and measuring processes are reliable.

Each PEDOT-based sensor, associated with the data of plot 1200, was produced as follows. A commercially available PEDOT:PSS suspension, having a concentration of 1-6% PEDOT:PSS in water, was diluted in dimethyl formamide to form an intermediate polymer solution having a concentration of 0.06-0.08 weight percent of PEDOT:PSS. The dimethyl formamide causes PEDOT:PSS to solubilize in this intermediate polymer solution. Next, glycerol triacetate was added to the intermediate polymer solution, for example at a level of 20-40 microliters of glycerol triacetate per 2 milliliters of the intermediate polymer solution. The resulting solution was ink-jet printed onto a glass substrate over a pair of interdigitated electrodes. Evaporation of the ink-jet printed solution formed a smooth polymer film substantially composed of PEDOT:PSS and glycerol triacetate. The smooth polymer film had a thickness of approximately 50 nanometers.

It is understood that other concentrations than those used in the specific process to make the sensors of FIG. 12 may provide good sensor performance. For example, the concentration of PEDOT:PSS in the intermediate polymer solution may be in the range between 0.02% and 0.2%, and glycerol triacetate may be added to the intermediate polymer solution to yield a concentration of glycerol triacetate in the range between 0.05% volume and 0.2% volume. In the smooth polymer film of the sensors, the ratio of PEDOT:PSS to glycerol triacetate may be in the range between 0.1 and 10 percent volume.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present systems and methods, which, as a matter of language, might be said to fall therebetween.

What is claimed is:

1. A sensor for sensing diols and triols, comprising:
a substrate;
a conductive coating disposed on the substrate and having affinity for binding with a substance selected from the group consisting of diols, triols, and a combination thereof, wherein the conductive coating comprises PEDOT:PSS, and wherein the conductive coating further comprises a humectant, said humectant being intermixed with the PEDOT:PSS; and
two electrodes in contact with the conductive coating to probe conductivity of the conductive coating so as to detect the substance from a reduction in the conductivity.

2. The sensor of claim 1, the substance being airborne.

3. The sensor of claim 1, the PEDOT:PSS and the humectant constituting at least 95 weight percent of the conductive coating.

4. The sensor of claim 3, thickness of the conductive coating being in the range between 20 and 1000 nanometers.

5. The sensor of claim 1, the humectant being glycerin triacetate.

6. The sensor of claim 5, the PEDOT:PSS and the glycerin triacetate constituting at least 95 weight percent of the conductive coating.

7. The sensor of claim 6, ratio of PEDOT:PSS to glycerin triacetate being in the range from 0.1 to 10 percent volume.

8. The sensor of claim 1, the conductive coating further including boronic acid.

9. The sensor of claim 1, the conductive coating being functionalized with boronic acid.

10. The sensor of claim 9, the boronic acid being 4-mercaptophenylboronic acid.

11. The sensor of claim 1, the conductive coating comprising metal nanoparticles functionalized with boronic acid.

12. The sensor of claim 11, the metal nanoparticles including gold nanoparticles.

13. The sensor of claim 11, the metal nanoparticles, together with boronic acid functionalized thereto, constituting at least 95 weight percent of the conductive coating.

14. The sensor of claim 13, thickness of the conductive coating being in the range between 10 and 2000 nanometers.

15. The sensor of claim 1, the conductive coating comprising carbon nanotubes functionalized with boronic acid.

16. The sensor of claim 1, the conductive coating comprising a conductive polymer functionalized with boronic acid.

17. The sensor of claim 1, the electrodes being interdigitated and disposed between the substrate and the conductive coating.

18. A sensor for sensing diols and triols, comprising:
a substrate;
a conductive coating disposed on the substrate and having affinity for binding with a substance selected from the group consisting of diols, triols, and a combination thereof; and
two electrodes in contact with the conductive coating to probe conductivity of the conductive coating so as to detect the substance from a reduction in the conductivity,
wherein the conductive coating comprises metal nanoparticles functionalized with boronic acid, said metal nanoparticles, together with boronic acid functionalized thereto, constituting at least 95 weight percent of the conductive coating.

* * * * *